United States Patent
Petraitis et al.

(10) Patent No.: US 8,895,785 B2
(45) Date of Patent: Nov. 25, 2014

(54) PROCESSES FOR SEPARATING ONE OR MORE AMINE BYPRODUCTS FROM ONE OR MORE DESIRED AMINES

(75) Inventors: David M. Petraitis, Covington, LA (US); Stephen W. King, League City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/996,997

(22) PCT Filed: Dec. 6, 2011

(86) PCT No.: PCT/US2011/063373
§ 371 (c)(1),
(2), (4) Date: Jun. 21, 2013

(87) PCT Pub. No.: WO2012/087553
PCT Pub. Date: Jun. 28, 2012

(65) Prior Publication Data
US 2013/0274522 A1    Oct. 17, 2013

Related U.S. Application Data

(60) Provisional application No. 61/425,365, filed on Dec. 21, 2010.

(51) Int. Cl.
*C07C 209/84* (2006.01)
*C07C 209/86* (2006.01)

(52) U.S. Cl.
CPC ............. *C07C 209/84* (2013.01); *C07C 209/86* (2013.01)
USPC ........................................................ 564/498

(58) Field of Classification Search
CPC .... C07C 209/84; C07C 209/86; C07C 209/90
USPC ........................................................... 564/498
See application file for complete search history.

(56) References Cited

U.S. PATENT DOCUMENTS

| | | | |
|---|---|---|---|
| 3,038,904 A | 6/1962 | Godfrey | |
| 3,193,472 A * | 7/1965 | Isacks, Jr. | 203/49 |
| 4,032,411 A | 6/1977 | Tornquist et al. | |
| 4,217,308 A | 8/1980 | Bernady et al. | |
| 4,906,782 A | 3/1990 | Hara et al. | |
| 4,911,793 A | 3/1990 | Mueller et al. | |
| 2006/0281951 A1 * | 12/2006 | Lee et al. | 564/511 |
| 2010/0087684 A1 | 4/2010 | Do et al. | |

FOREIGN PATENT DOCUMENTS

| | | |
|---|---|---|
| JP | 0509777 | 4/1993 |
| WO | WO 2006/114417 | 11/2006 |
| WO | WO 2009/083580 | 7/2009 |
| WO | WO 2010/042160 | 4/2010 |
| WO | WO 2010/042168 | 4/2010 |

* cited by examiner

*Primary Examiner* — Brian J Davis
(74) *Attorney, Agent, or Firm* — Kagan Binder, PLLC

(57) ABSTRACT

The present invention relates to separating one or more amine byproducts from one or more desired amines. More particularly, the invention involves forming a byproduct component with one or more amine byproducts and a first adjuvant component. The byproduct component has an enhanced separation characteristic relative to separating the amine byproducts from the desired amines in the absence of an adjuvant. Preferably, the byproduct component is separated in the presence of a second adjuvant component that preferably has a boiling point less than the boiling point of the first adjuvant component.

17 Claims, 3 Drawing Sheets

PROCESSES FOR SEPARATING ONE OR MORE AMINE BYPRODUCTS FROM ONE OR MORE DESIRED AMINES

This application claims benefit from International Application No. PCT/US2011/063373, filed Dec. 6,2011, having International Publication No WO 2012/087553, which in turn claims priority to U.S. Provisional Application Ser. No. 61/425,365, filed Dec. 21, 2010, entitled "PROCESSES FOR SEPARATING ONE OR MORE AMINE BYPRODUCTS FROM ONE OR MORE DESIRED AMINES" which applications are incorporated herein by reference in their entireties for all purposes.

FIELD

The present invention relates to separating one or more amine byproducts from one or more desired amines.

INTRODUCTION

Some processes used to manufacture desirable amines can produce mixtures of one or more desired amines and one or more amine byproducts such as alkylation byproducts. As an example, methylamine and ethylamine can be formed during the reductive amination of monoethanolamine with ammonia. The methylamine and ethylamine are capable of further reaction with ethanolamines or ethyleneamines to give several alkyl-ended ethyleneamines which are typically undesired. Thus, a mixture of desired ethyleneamines (e.g., ethylenediamine, and the like) and alkylethyleneamines (e.g., methylethylenediamine, ethylethylenediamine, and the like) are produced.

Recovery of desired amities from a mixture that includes amine byproducts, such as effluent(s) from the manufacture of desired amines, can be extremely difficult and costly because one or more of the amine byproducts can have boiling points very close to the boiling points of the desired amines and/or can form close-boiling azeotropes.

Accordingly, there is a continuing need to find useful methods of separating desired amines from amine byproducts.

SUMMARY

The present invention involves causing a mixture of desired amine(s) and amine byproduct(s) to be in contact with a first adjuvant component so as to form a byproduct component. The byproduct component has an enhanced separation characteristic with respect to separating the amine byproducts from the desired amines. Preferably, the byproduct component is separated from the mixture of desired amines and amine byproducts in the presence of a second adjuvant component that preferably has a boiling point less than the boiling point of the first adjuvant component. Advantageously, in some embodiments a process according to the present invention can permit the separation to be performed at relatively lower temperatures and/or pressures, which can save in operating costs. As another advantage, in some embodiments a process according to the present invention can permit substantially all or most of the amine byproducts, the first adjuvant, and optionally the second adjuvant to be removed in a single distillation column such that additional column(s) can be eliminated if desired.

According to an aspect of the present invention, a process for separating one or more amine byproducts from one or more desired amines comprising the steps of:

a) providing a composition comprising i) one or more desired amines and one or more amine byproducts and ii) a first adjuvant component, wherein the first adjuvant component has a boiling point;

b) causing the composition to be subjected to conditions such that at least a portion of the one or more amine byproducts and at least a portion of the first adjuvant component form a byproduct component that has an enhanced separation characteristic relative to the one or more amine byproducts that have not been subjected to said conditions; and c) separating at least a portion of the byproduct component from the composition in the presence of a second adjuvant component.

According to another aspect of the present invention, a process for separating one or more alkylethyleneamines from one or more ethyleneamines comprising the steps of:

a) providing a composition comprising i) one or more ethyleneamines and one or more alkylethyleneamines and a first adjuvant component comprising water, wherein the first adjuvant component has a boiling point;

b) causing the composition to be subjected to conditions such that at least a portion of the one or more alkylethyleneamines and at least a portion of the first adjuvant component form an alkylethyleneamines component that has an enhanced separation characteristic relative to the one or more alkylethyleneamines that have not been subjected to said conditions; and c) separating at least a portion of the alkylethyleneamines component from the composition in the presence of a second adjuvant component.

According to another aspect of the present invention, a process for separating one or more amine byproducts from one or more desired amines comprising the steps of:

a) providing a composition comprising i) one or more desired amines and one or more amine byproducts and ii) a first adjuvant component, wherein the composition does not include water in an amount of more than one percent by weight of the total composition;

b) causing the composition to be subjected to conditions such that at least a portion of the one or more amine byproducts and at least a portion of the first adjuvant component form a byproduct component that has an enhanced separation characteristic relative to the one or more amine byproducts that have not been subjected to said conditions; and c) separating at least a portion of the byproduct component from the composition.

BRIEF DESCRIPTION OF THE DRAWINGS

The advantages of the present invention, and the manner of attaining them, will become more apparent and the invention itself will be better understood by reference to the following description of the embodiments of the invention taken in conjunction with the accompanying drawing, wherein.

DETAILED DESCRIPTION

Figure 1:
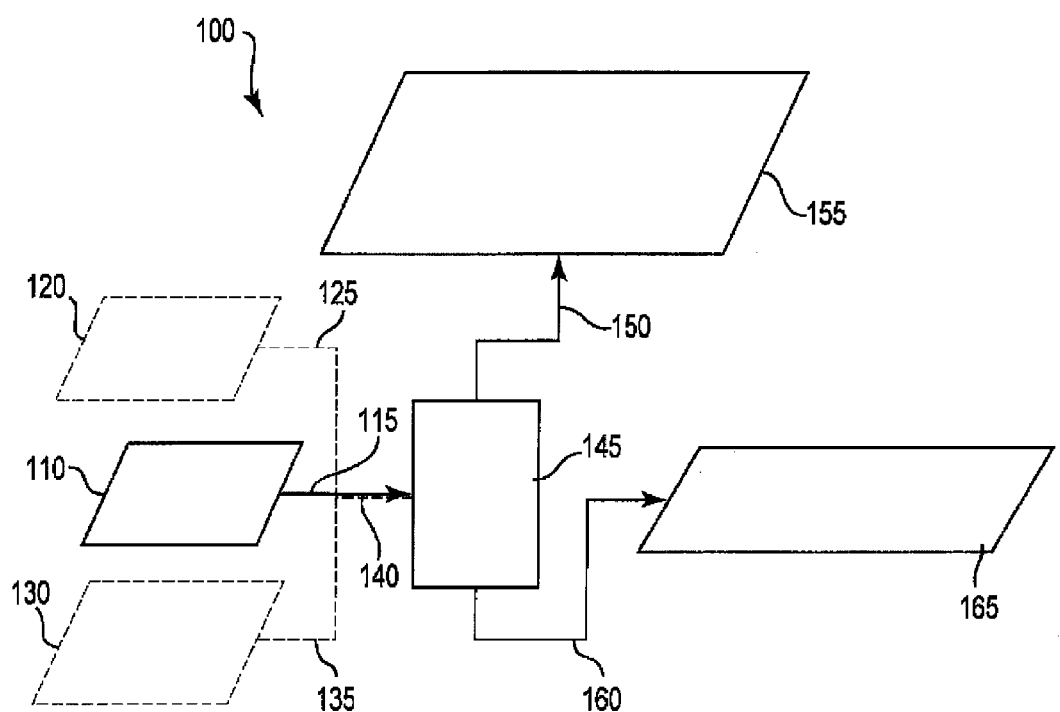
FIG. 1 shows a block diagram schematically illustrating a system for separating ethyleneamines from alkylethyleneamines according to an embodiment of the present invention.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides methods for separating one or more amine byproducts from one or more desired amines.

As used herein, the term "amine" refers to an organic compound that includes at least one amine moiety. In some embodiments, an amine refers to an organic compound that includes at least two amine moieties, at least three amine moieties, or even at least four amine moieties. Amines that include two or more amine moieties are referred to herein as polyamines. An organic compound as used herein refers to a compound that includes at least one carbon atom and at least one hydrogen atom that is covalently bound to a carbon atom or that is covalently bound to an oxygen atom that is covalently bound to a carbon atom. The amine compounds may be linear, branched, cyclic, or acyclic, saturated, unsaturated, aliphatic, and/or aromatic.

A composition that can be separated according to the present invention includes one or more desired amines. As used herein, "desired" amines means any one or more amines that are desired to be separated from one or more amine byproducts (discussed below). An exemplary class of desired amines includes alkyleneamines. Exemplary alkyleneamines can be represented by the following formula (I):

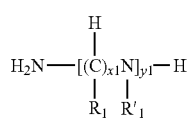

(I)

wherein $x_1$ is a number of from 2 to 6, $y_1$ is a number of from 1 to 6, $R_1$ represents a hydrogen atom or an alkyl group having 1 to 4 carbon atoms, and $R'_1$ represents a group represented by the following formula (1):

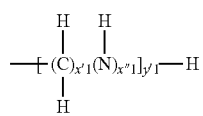

(1)

wherein $x'_1$ is a number of from 2 to 6, $x''_1$ is 0 or 1 and $y'_1$ is a number of from 0 to 4. Exemplary alkyleneamines may also be represented by the following formula (II):

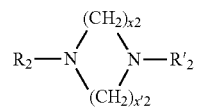

(II)

wherein $x_2$ and $x'_2$ are numbers of from 2 to 6, and $R_2$ and $R'_2$ represent a group represented by the following formula (2):

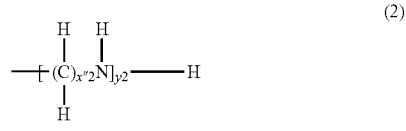

(2)

wherein $x''_2$ is a number of from 2 to 6 and $y_2$ is a number of from 0 to 5. One or more compounds represented by the formula (I) and the formula (II) can be used. An exemplary class of desired alkyleneamines includes ethyleneamines. Another exemplary class of desired amines includes ethanolamines.

Examples of desired amines include monoethanolamine (also referred to as ETA, MEA, or MEOA), diethanolamine (also referred to as DEA or DEOA), triethanolamine (also referred to as TEA or TEOA), 1,3-diaminopropane (1,3-DAP), dipropylenetriamine, 1,3-pentanediamine, 1,3-butanediamine, 2,2-dimethyl-1,3-propanediamine, 2,2-diethyl-1,3-propanediamine, ethylenediamine (EDA), diethylenetriamine (DETA), triethylenetetramine (TETA), tetraethylenepentamine (TEPA), piperazine (PIP), aminoethylpiperazine (AEP), aminoethylethanolamine (AEEA), heavy polyamine (HPA), combinations of these and the like. HPA is a mixture of linear, branched, and/or cyclic ethyleneamines, the structures of which can be deduced from the chemistry of manufacture and knowledge of the structures present in TETA and TEPA. The structures of the principle components of HPA can contain six or more nitrogen atoms per molecule.

The one or more desired amines can be obtained from any desirable source. For example, the one or more desired amines can be synthesized to form an effluent that contains the one or more desired amines. In some embodiments, one or more effluents of desired amines can be combined together to form a composition including desired amines. As another example, individual desired amines can be mixed together to form a composition including desired amines. As still another example, one or more individual desired amines can be added to one or more effluents to form a composition including desired amines.

Methods of producing desired amines are well known. Exemplary amine production processes include reductive amination, transamination, combinations of these, and the like.

Transamination is well known and involves a transfer of an amino group from one chemical compound to another, or the transposition of an amino group within a chemical compound. As an example, WO 2010/042160 (Cook et al.) discloses generating one or more ethyleneamines by reacting ethylenediamine with one or more additional ethyleneamines in the presence of a transamination catalyst.

Reductive amination is another process by which amines are produced. Reductive amination is generally described as the conversion of a carbonyl group (e.g., aldehydes and ketones) to an amine via an intermediate imine. In addition to carbonyl groups, other compounds which can undergo reductive amination include derivatives containing one or more functional groups such as hydroxyl, amino, imino or combinations thereof. As an example, WO 2010/042168 (Do et al.) discloses generating alkylamines via reductive amination of ethanolamines and ammonia to form ethyleneamines.

As yet another example of making desired amines, one or more ethanolamines can be manufactured by reacting ethylene oxide with ammonia. Illustrative of such processes are those described in U.S. Pat. No. 4,400,539 (Gibson et al.) and PCT Publication Number WO 2006/114417.

Methods of the producing desired amines in connection with the invention can be practiced in any suitable reactor. These include batch reactors, continuous fixed bed reactors, slurry bed reactors, fluidized bed reactors, catalytic distillation reactors, combinations of these, and the like.

In some embodiments, before separating the amine byproduct(s) from the desired amine(s) according to the present invention, the desired amine(s) can be present in amount of from 90 to 99.999 percent by weight of the total composition, from 95 to 99.999 percent by weight of the total composition, from 99 to 99.99 percent by weight of the total composition, or from 99.1 to 99.9 percent by weight of the total composition.

A composition that can be separated according to the present invention includes one or more amine byproducts. As used herein "amine byproduct" means any amine that is a byproduct in the production of a desired amine. It is noted that an amine byproduct does not necessarily need to be produced along with the desired amine that is to be separated. For example, the amine byproduct(s) could be produced separately from the desired amine(s) and subsequently mixed together before separating them according to the present invention. An exemplary class of amine byproducts includes alkylalkyleneamines and an exemplary class of alkylalkyleneamines includes alkylethyleneamines.

Amine byproduct(s) can be obtained from any desirable source. For example, the amine byproducts can be synthesized and present in an effluent (typically along with desired amines, impurities, and/or other byproducts) that contains the one or more amine byproducts. In some embodiments, one or more effluents of amine byproducts can be combined together to form a composition including amine byproducts. As another example, individual amine byproducts can be mixed together to form a composition including amine byproducts. As still another example, one or more individual amine byproducts can be added to one or more effluents to form a composition including amine byproducts.

Exemplary amine byproduct production processes include reductive amination, transamination, combinations of these, and the like, which are described above with respect to producing desired amines. Typically, production of the amine byproducts occurs in the same processes that form the desired amines.

Amine byproducts can be provided as alkylation byproducts from one or more processes that produce the desired amine(s).

Examples of amine byproducts include methylethylenediamine, ethylethylenediamine, methyldiethylenetriamine, ethyldiethylenetriamine, etc., and combinations of these.

In some embodiments, before separating the amine byproduct(s) from the desired amine(s) according to the present invention, the amine byproduct(s) can be present in amount of from 10 to 0.001 percent by weight of the total composition, from 5 to 0.001 percent by weight of the total composition, from 1 to 0.01 percent by weight of the total composition, or from 0.9 to 0.1 percent by weight of the total composition.

A composition that can be separated according to the present invention includes a first adjuvant component. As used herein, a "first adjuvant component" refers to a first component including one or more adjuvants. An "adjuvant" as used herein with respect to the first adjuvant component (and second adjuvant component discussed below) refers to any chemical substance contained in or added to a product mixture to aid in the separation of one or more compounds. A first adjuvant component according to the present invention can help form a "byproduct component" (discussed below) that has an enhanced separation characteristic with respect to separating one or more desired amines from one or more amine byproducts. While not being bound by theory, it is believed that under proper conditions the first adjuvant component helps form a byproduct component that is enriched with the one or more amine byproducts relative to the one or more desired amines such that the separation of the byproducts from the desired amines is enhanced as compared to not including a first adjuvant component. Accordingly, a first adjuvant component adjuvant can be selected by considering at least the one or more desired amities and/or one or more amine byproducts that are to be separated from each other.

In some embodiments, the boiling point of the first adjuvant component can also be considered when selecting individual adjuvant(s). The boiling point of the first adjuvant component can be selected to be less than the boiling point of the one or more amine byproducts, the one or more desired amines, and combinations of these. For example, in the context of separation by distillation, having the boiling point of the first adjuvant component less than the desired amines and amine byproducts can facilitate reducing the temperature necessary for separating the amine byproducts from the desired amines. In such a situation, the first adjuvant component portion that is enriched with the amine byproducts can be carried in an overhead distillation product stream. Alternatively, the boiling point of the first adjuvant component can be selected so that at least a portion or substantially all of the byproduct component remains in the reboiler and/or is carried in a bottom distillation product stream while the overhead distillation product stream is enriched with the desired amines.

Preferably, the boiling point of the first adjuvant component has a boiling point that is substantially less than the boiling point of the desired amines so as to facilitate separation between the first adjuvant component and the desired amines should any of the first adjuvant component remain with the desired amines after the desired amities have been separated from the amine byproducts to a satisfactory degree.

Examples of adjuvants that can be included in first adjuvant component include water, one or more hydrocarbons, lower alkylene glycols, monoalkyl ethers of alkylene glycol, dialkyl ethers of alkylene glycol, lower aliphatic alcohols, and combinations thereof.

In some embodiments, a preferred adjuvant includes water. For example, because water can be produced as a byproduct in the production of a desired amine (e.g., in reductive amination of monoethanolamine with ammonia) water is already present in the effluent so using water as an adjuvant can be efficient.

In other embodiments, water as an adjuvant can be excluded. In such embodiments, the composition including desired amines and amine byproducts does not include water in an amount of more than one percent by weight of the total composition. Such an insignificant amount of water may be present because amines can be hydrophilic and, therefore, tend to attract water. However, permitting such an insignificant amount of water in the composition does not function as an adjuvant as described herein.

In some embodiments, the first adjuvant component does not include alcohol. For example, in some embodiments, the first adjuvant component does not include ethanol.

In some embodiments, the first adjuvant component does not include a hydrocarbon solvent. Examples of hydrocarbon solvents that can be excluded from the first adjuvant component include n-heptane, isooctane, cyclohexane, n-hexane, methylcyclohexane, n-pentane, and combinations thereof.

The adjuvant(s) for use in the first adjuvant component can be obtained from any desirable source. For example, the adjuvant(s) can be present in an effluent (typically along with desired amines, impurities, and/or amine byproducts) from producing desired amines. In some embodiments, one or more effluents that include at least a portion of the first adjuvant component can be combined together to form a composition including the first adjuvant component. As another example, individual adjuvants can be mixed together to form a composition including the first adjuvant component. As still another example, one or more individual adjuvants can be added to one or more effluents to form a composition including the first adjuvant component.

In some embodiments, before separating the amine byproduct(s) from the desired amine(s) according to the present invention, the first adjuvant component can be present in amount of from 0.1% to 50% by weight of the total composition, from 1.5% to 35% by weight of the total composition, or from 2.5% to 20% by weight of the total composition.

Optionally, a composition that can be separated according to the present invention can include a second adjuvant component. As used herein, a "second adjuvant component" refers to a second component including one or more adjuvants that can help form a "byproduct component" (discussed below) that has an enhanced separation characteristic with respect to separating one or more desired amines from one or more amine byproducts. While not being bound by theory, it is believed that under proper conditions the second adjuvant component also helps form a byproduct component that is enriched with the one or more amine byproducts relative to the one or more desired amines such that the separation of the desired amines from the byproducts is enhanced as compared to not including a second adjuvant component. A second adjuvant component can be selected by considering one or more of the desired amines, the amine byproducts, and/or the first adjuvant component.

The boiling point of the second adjuvant component can also be considered when selecting individual adjuvant(s). In some embodiments, the boiling point of the second adjuvant component can be selected to be less than the boiling point of the one or more amine byproducts, the one or more desired amines, the first adjuvant component, and combinations of these. For example, having the boiling point of the second adjuvant component less than the first adjuvant component can facilitate reducing the temperature necessary for separating at least a portion of the amine byproducts from at least a portion of the desired amines. In the context of distillation, the overhead distillation product stream is preferably enriched with the amine byproducts. Alternatively, the boiling point of the second adjuvant component can be selected so that at least a portion or substantially all of the byproduct component remains in the reboiler and/or is carried away in a bottom distillation product stream while the overhead distillation product stream is enriched with the desired amines.

Preferably, the boiling point of the second adjuvant component has a boiling point that is substantially less than the boiling point of the first adjuvant component so as to facilitate separation between the first adjuvant component and the second adjuvant component if desired.

Preferably, the second adjuvant component is effectively inert in the separation process so as to not cause any undesirable reaction(s) to an undue degree.

Examples of adjuvants that can be included in second adjuvant component include ammonia, diatomic hydrogen, diatomic nitrogen, methane, methylamine, ethylamine, carbon dioxide, and combinations thereof. In some embodiments, ammonia is preferably included in the second adjuvant component because ammonia can already be present in the effluent from one or more processes that make the one or more desired amines and one or more amine byproducts.

In some embodiments, water as an adjuvant can be excluded. In such embodiments, the composition including desired amines and amine byproducts does not include water in an amount of more than one percent by weight of the total composition. Such an insignificant amount of water may be present because amines can be hydrophilic and, therefore, tend to attract water. However, permitting such an insignificant amount of water in the composition does not function as an adjuvant as described herein.

The adjuvant(s) for use in the second adjuvant component can be obtained from any desirable source. For example, the adjuvant(s) can be present in an effluent (typically along with desired amines, impurities, amine byproducts, and/or the first adjuvant component) from producing desired amines. In some embodiments, one or more effluents that include at least a portion of the second adjuvant component can be combined together to form a composition including the second adjuvant component. As another example, individual adjuvants can be mixed together to form a composition including the second adjuvant component. As still another example, one or more individual adjuvants can be added to one or more effluents to form a composition including the second adjuvant component.

In some embodiments, before separating the amine byproduct(s) from the desired amine(s) according to the present invention, the second adjuvant component can be present in amount of from 0.1% to 65% by weight of the total composition, from 1% to 55% by weight of the total composition, or from 2% to 10% by weight of the total composition.

Optionally, a composition that can be separated according to the present invention can include one or more additional compounds.

A composition that can be separated according to the present invention can be provided in any desired manner. The compounds of the composition can be obtained individually, already combined (e.g., from one or more process effluents), and combinations thereof. A single effluent stream can be subjected to separation process(es) according to the present invention or one or more different sources can be combined to form the composition to be subjected to a separation process according to the present invention. If multiple sources are combined together to form the composition to be separated, the timing of combining the sources can be any desired timing sequence as long as the byproduct component can be formed for separation purposes. For example, one or more effluent streams can be combined with one or more additional streams to form the composition to be separated. One or more of the effluent streams may contain the desired amines, the amine byproducts, and, optionally, at least a portion (or substantially all) of the first adjuvant component and/or at least a portion (or substantially all) of the second adjuvant component. The one or more additional streams could include at least a portion (or substantially all) of the first adjuvant component, at least a portion (or substantially all) the second adjuvant component, additional compounds, and combinations thereof. When multiple streams/sources are combined to form the composition to be separated, one or more may be combined prior to the separation process (e.g., prior to entering a distillation column) and one or more may be combined during the separation process (e.g., combined within a distillation column).

To help separate the desired amines from the amine byproducts, at least a portion of the one or more amine byproducts is caused to contact at least a portion of the first adjuvant under conditions that form a "byproduct component" having an "enhanced separation characteristic."

As used herein, a "byproduct component" refers to a component of the composition that is formed as a result of at least a portion of the first adjuvant component (and optionally at least a portion of the second adjuvant component) and at least a portion of the one or more amine byproducts being in contact under proper conditions. When subjected to proper conditions, the byproduct component is enriched with the one or more amine byproducts relative to the one or more desired amines so as to enhance the separation of the one or more desired amines from the byproducts. The byproduct component can improve the separation of amine byproducts from desired amines as compared to if the amine byproduct were not in contact with the first adjuvant component (and optionally the second adjuvant component) under proper conditions.

As used herein an "enhanced separation characteristic" means that the amine byproducts are more readily separated from the desired amines than if the amine byproducts had not formed a byproduct component with the first adjuvant (and optionally, at least a portion of the second adjuvant component). That the amine byproducts can be more readily separated can mean one or more of the following: more amine byproducts can be separated from the desired amines for a given set of conditions or the amine byproducts can be separated from the desired amines at a lower temperature and/or pressure. While not being bound by theory, it is believed the amine byproducts become more enriched in the first adjuvant component (and optionally the second adjuvant component) by forming an admixture such as an azeotrope and/or becoming entrained in the first adjuvant component.

As used herein, an "azeotrope" refers to a constant boiling mixture having vapor and liquid compositions of the same composition. By forming an admixture such as an azeotrope and/or entraining the amine byproducts in the first adjuvant component permits a concentration gradient to be formed among the desired amines and amine byproducts such that the amine byproducts can be separated from the desired amines.

At least a portion of the byproduct component can be separated from the composition, preferably in the presence of a second adjuvant component, so as help separate amine byproducts from desired amines. Any conventional separations technology that can take advantage of a byproduct component as described herein and separate chemical constituents having varying physical properties can be used to separate the amine byproducts from the desired amines according to the present invention. Exemplary separation systems include distillation, dividing wall column, multiple single stage separators, compressors, chillers, absorbers, combinations of these, and the like.

According to the present invention, conditions are selected to form a byproduct component having an enhanced separation characteristic and separate at least a portion of the byproduct from the desired amines. Selected conditions may include one or more of temperature, pressure, and compositional ratios. For example, in the context of distillation, a column can be operated in a fashion such that maximum interaction between the first adjuvant component (and optionally the second adjuvant component) and the amine byproduct(s) is obtained. This can be accomplished by selecting column temperature and pressure for a given feed stream(s) to realize maximum separation of the byproduct component from the desired amine. Temperature and pressure within the column can be established to provide the appropriate concentration of adjuvant component(s), amine byproduct(s), and desired amine(s) to affect the separation.

As an example, selected conditions for a distillation column are discussed below.

An exemplary distillation column can include between 2 and 200 theoretical separation stages with between 1 and 199 theoretical rectifying stages and between 1 and 199 theoretical stripping section stages. Preferably, a distillation column can include between 2 and 100 theoretical separation stages with between 1 and 99 theoretical rectifying stages and between 1 and 99 theoretical stripping section stages. Even more preferred, a distillation column can include between 2 and 50 theoretical separation stages with between 1 and 25 theoretical rectifying stages and between 1 and 25 theoretical stripping section stages. The separation stages can be formed using any trays or packing.

An exemplary distillation column can also have a reboiler and condenser and the optional ability to feed multiple feeds throughout the column (for example, the ability to feed material to the condenser, the top stage of the rectifying section, in the middle of the rectifying section, to the transition between rectifying and stripping sections and approximately in the middle of the stripping section).

Exemplary temperatures for the reboiler include a temperature in the range of from 100° C. to 250° C., preferably from 150° C. to 220° C. Preferably, the reboiler operates at a temperature below 200° C.

Exemplary temperatures for the condenser include a temperature the range of from at −33° C. to 120° C., preferably from 15° C. to 120° C. Preferably, the condenser operates at a temperature at or above 40° C.

An exemplary distillation column can operate at a pressure in a range of from 26 kPa (200 mm Hg) to 621 kPa (75 PSIG), preferably from 101 kPa (0 PSIG) to 621 kPa (75 PSIG), and even more preferably from 172 kPa (10 PSIG) to 379 kPa (40 PSIG).

Optionally, one or more separation steps can be used to further refine any of the product compositions that result after a step of separating according to the present invention.

In some embodiments, a single step of separating may separate the desired level (e.g., substantially all) of the desired amines from the amine byproducts. Advantageously, such a separation process could use a single separation unit operation to achieve satisfactory separation results. Eliminating a unit operation such as a distillation column is very significant in terms of cost savings. An example of such an embodiment is discussed below in connection with FIG. 3.

In other embodiments, multiple separating steps according to the present invention may be employed to separate the desired level (e.g., substantially all) of the desired amines from the amine byproducts. Advantageously, such a separation process could be used to retrofit an existing system of unit operations to achieve satisfactory separation results. An example of such an embodiment is discussed below in connection with FIG. 2.

After separating at least a portion of the byproduct component from the desired amines, an "amine byproduct enriched composition" is produced that is relatively enriched in the amine byproducts as compared to the desired amines. The amine byproduct enriched composition includes at least a portion of the amine byproducts, at least a portion of the first adjuvant component, and, optionally, at least a portion of the second adjuvant component and/or a relatively small portion of the desired amines.

In some embodiments, after separation, the amine byproduct enriched composition can include from 5 to 100 percent by weight of the amine byproducts that were present in the composition to be separated, from 50 to 100 percent by weight of the amine byproducts that were present in the composition to be separated, or even from 90 to 100 percent by weight of the amine byproducts that were present in the composition to be separated.

In some embodiments, after separation, the amine byproduct enriched composition can include from 51 to 100 percent by weight of the first adjuvant component that was present in the composition to be separated, from 75 to 100 percent by weight of the first adjuvant component that was present in the composition to be separated, or even from 90 to 100 percent by weight of the first adjuvant component that was present in the composition to be separated.

In some embodiments, after separation, the amine byproduct enriched composition can include from 51 to 100 percent by weight of the second adjuvant component that was present in the composition to be separated, from 75 to 100 percent by weight of the second adjuvant component that was present in the composition to be separated, or even from 98 to 100 percent by weight of the second adjuvant component that was present in the composition to be separated.

In some embodiments, after separation, the amine byproduct enriched composition can include from 0 to 25 percent by weight of the desired amines that were present in the composition to be separated, from 0 to 10 percent by weight of the desired amines that were present in the composition to be separated, or even from 0 to 2 percent by weight of the desired amines that were present in the composition to be separated.

Also, after separating at least a portion of the byproduct component from the desired amines, a "desired amines enriched composition" is produced that is relatively enriched in the desired amines as compared to the amine byproducts. The desired amines enriched composition includes at least a portion of the desired amines and, optionally, at least a portion of the first adjuvant component, at least a portion of the second adjuvant component, and/or a relatively small portion of the amine byproducts.

In some embodiments, after separation, the desired amines enriched composition can include from 75 to 100 percent by weight of the desired amines that were present in the composition to be separated, from 90 to 100 percent by weight of the desired amines that were present in the composition to be separated, or even from 98 to 100 percent by weight of the desired amines that were present in the composition to be separated.

In some embodiments, after separation, the desired amines enriched composition can include from 0 to 49 percent by weight of the first adjuvant component that was present in the composition to be separated, from 0 to 25 percent by weight of the first adjuvant component that was present in the composition to be separated, or even from 0 to 10 percent by weight of the first adjuvant component that was present in the composition to be separated. As an example, when the first adjuvant component includes water, after separation the desired amines enriched composition can include water in an amount of 2, 1, or even 0.5 percent or less by weight of the desired amines enriched composition.

In some embodiments, after separation, the desired amines enriched composition can include from 0 to 49 percent by weight of the second adjuvant component that was present in the composition to be separated, from 0 to 25 percent by weight of the second adjuvant component that was present in the composition to be separated, or even from 0 to 2 percent by weight of the second adjuvant component that was present in the composition to be separated. As an example, when the second adjuvant component includes ammonia, after separation the desired amines enriched composition can include ammonia in an amount of 0.1, 0.05, or even 0.01 percent or less by weight of the desired amines enriched composition.

In some embodiments, after separation, the desired amines enriched composition can include from 0 to 95 percent by weight of the amine byproducts that were present in the composition to be separated, from 0 to 50 percent by weight of the amine byproducts that were present in the composition to be separated, or even from 0 to 2 percent by weight of the amine byproducts that were present in the composition to be separated. As an example, when the amine byproducts include alkylethyleneamines, after separation the desired amines enriched composition can include alkylethyleneamines in an amount of 0.5, 0.2, or even 0.1 percent or less by weight of the desired amines enriched composition.

Optionally, one or more additional processes can be employed to further modify/refine the compositions that are obtained after the separating step(s) according to the present invention to separate the desired amines from the amine byproducts. For example, water may form an azeotrope with one or more of the desired amities so it may be desirable to separate the azeotropic water from the desired amines. Such methods are known and are disclosed in U.S. Pat. No. 4,032,411 (Tornquist et al.) and WO 2010/042168 (Do et al.).

As another example, after separating the desired amines from the amine byproducts, the desired amines can be separated from each other by any method known in the art. Examples of methods of separating desired amities from each other include conventional distillation technology among other well known separation techniques.

Also, optionally, at least a portion of one or more compositions that are obtained after the separating step(s) according to the present invention can be recovered and recirculated if desired. For example, at least a portion of the first adjuvant component and/or at least a portion of the second adjuvant component can be recovered and recirculated if desired.

Exemplary embodiments of separating amine byproducts from desired amines according to the present invention are discussed below in connection with FIGS. 1-3 in the context of separating ethyleneamines as desired amines from alkylethyleneamines as amine byproducts.

FIG. 1 shows a block diagram schematically illustrating a system 100 for separating amine byproduct(s) from desired amine(s) according to one embodiment of the present invention. Source(s) 110 include crude amines containing desired amines (e.g., alkyleneamines and the like) and amine byproducts (e.g., alkylalkyleneamines and the like) and optionally ammonia, alkylamines, hydrogen, water, alkanolamines that are fed via stream 115. Typically, source(s) 110 can come from the effluent of a reductive amination reactor. In some embodiments, 10-99.9% of ammonia can first be removed. In other embodiments, stream 115 can be a refined stream consisting mainly of the desired amines and amine byproducts.

Source(s) 120 can include at least a portion of the first adjuvant component. The dotted line 125 indicates that source(s) 120 are optional. For example, if stream 115 does not have enough of the first adjuvant component present, source(s) 120 can provide substantially all or an additional amount of the first adjuvant component so as to help form a byproduct component as described herein. Stream 125 can be combined with stream 115 before entering unit operation 145 or within unit operation 145. Optionally, the composition of stream 125 can be substantially the same as stream 115.

Source(s) 130 can include at least a portion of the optional second adjuvant component. The dotted line 135 indicates that source(s) 130 are optional. For example, if stream 115 does not have enough of the second adjuvant component present, source(s) 130 can provide substantially all or an additional amount of the second adjuvant component so as to help form a byproduct component as described herein. Stream 135 can be combined with stream 115 before entering unit operation 145 or within unit operation 145. Optionally, the composition of stream 135 can be substantially the same as stream 115.

Stream 140 represents the total feed to unit operation 145. As mentioned above, the streams 115, 125, and 135 can be combined before entering unit operation 145 and/or can be combined within unit operation 145. An example of a unit operation 145 includes a distillation column.

Stream 150 represents one or more streams that contain at least a portion of the byproduct component that is separated from the desired amines. The byproduct component includes at least a portion of the amine byproducts, at least a portion of the first adjuvant component, and, optionally at least a portion of the second adjuvant component and/or a relatively small portion of the desired amines. Stream(s) 150 can be delivered to any desired destination 155.

Stream 160 represents one or more streams that contain at least a portion of the desired amines that have had the amine byproducts at least partially removed. Stream 160 can be delivered to any desired destination 165 such as storage, additional processing, combinations of these, and the like.

Figure 2:
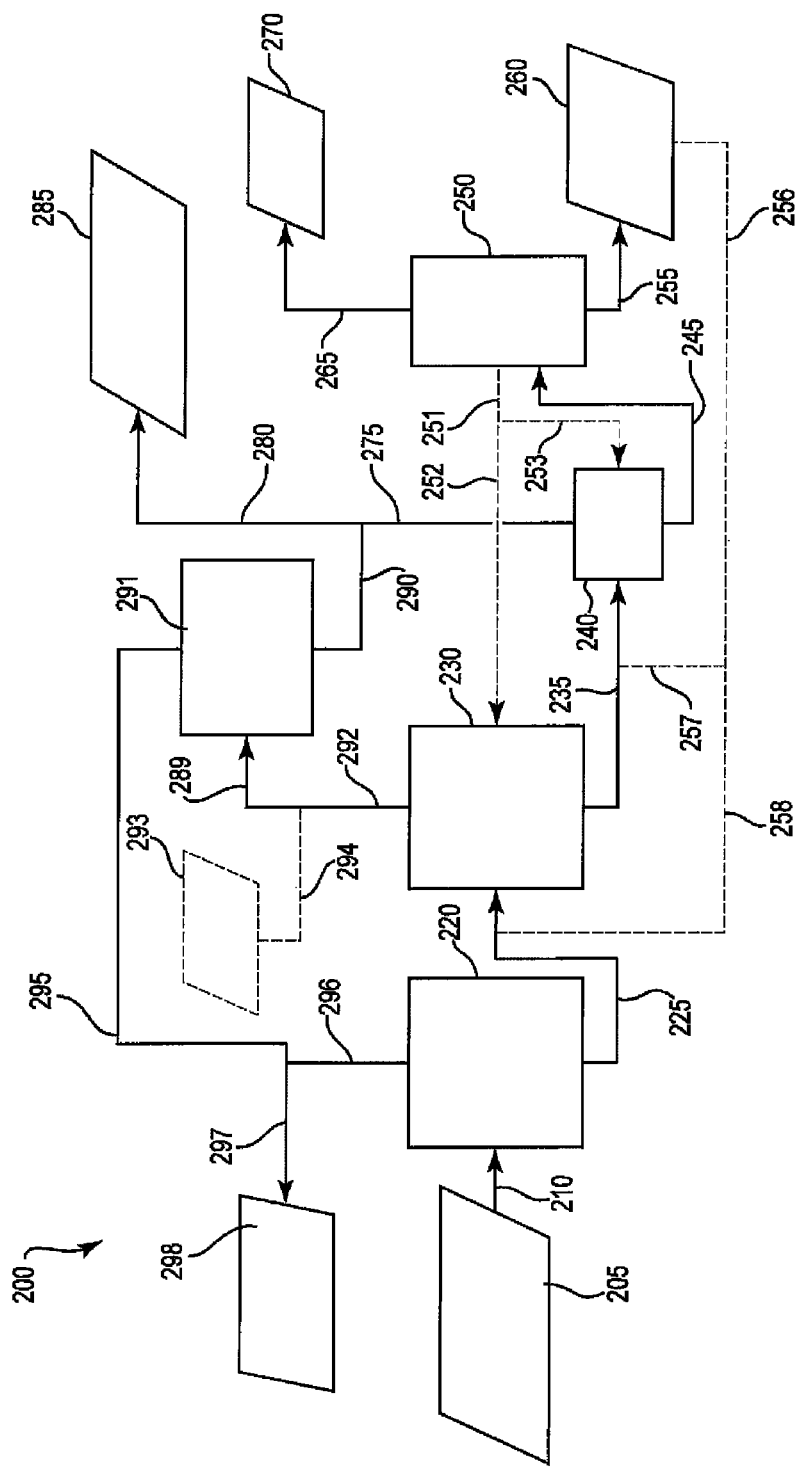
FIG. 2 shows a block diagram schematically illustrating a system for separating ethyleneamines from alkylethyleneamines according to another embodiment of the present invention.

FIG. 2 shows a block diagram schematically illustrating a system 200 for separating alkylethyleneamines from ethyleneamines according to another embodiment of the present invention. System 200 shows a conventional layout of unit operations for refining a crude ethyleneamines stream but operates distillation column 230 according to the present invention so as to enhance the removal of alkylethyleneamines. Conventional systems for refining crude amine streams are well known and are described in WO 2010/042168 (Do et al.).

A crude ethyleneamines stream 210 is provided from reactor 205. Stream 210 includes ethyleneamines, alkylethyleneamines, a first adjuvant component including water, and a second adjuvant component including ammonia. 220 represents flash tanks or an ammonia forecolumn, which operates to remove at least part of the ammonia.

Stream 225 is delivered to distillation column 230 which is operated according to the present invention to create a byproduct component that has an enhanced separation characteristic to help separate the alkylethyleneamines from the ethyleneamines. Stream 225 includes ethyleneamines, alkyethyleneamines, a first adjuvant component including water, and a second adjuvant component including ammonia. At least part of the alkylethyleneamines, water, and ammonia are separated from the ethyleneamines in column 230 and exit column 230 via stream 292.

The overhead stream 292 includes water; ammonia, and alkylethyleneamines. Stream 292 can optionally be combined with stream 294 from water source 293 to form stream 289. Stream 289 is delivered to an ammonia purification column 291. The overhead stream 295 includes ammonia (and does not include ethyleneamine) and can be combined with overhead stream 296 from flash tanks or forecolumn 220 and delivered to a recycle stream or reactor 298 via stream 297. Bottom stream 290 includes water and alkylethyleneamines.

Stream 235 is thus enriched in the ethyleneamines and is delivered to water column 240 so that additional water, and optionally alkylethyleneamines, can be separated from the ethyleneamines. The water in stream 235 typically forms an azeotrope with the ethyleneamines so water column 240 is preferably operated at conditions that so called break the azeotrope and permit substantially all of the water to be removed.

The overhead stream 275 includes water, and optionally alkylethyleneamines, and is combined with stream 290 to form stream 280 that can be delivered to waste treatment process 285.

Stream 245 is enriched in ethyleneamines and is delivered to column 250 for separating the ethyleneamines. Optionally, column 250 can remove any remaining water (typically with a small amount of one or more ethyleneamines since they can form an azeotrope with water) and recycle it via streams 251, 252, and 253. As an example, overhead stream 265 can include ethylenediamine (EDA) or EDA and piperazine (PIP) and be delivered to storage or final processing 270. Stream 255 can include heavier ethyleneamines that are delivered to additional refining processes 260. Optionally, at least a portion of the heavier ethyleneamines can be recycled via streams 256, 257, and/or 258.

Figure 3:
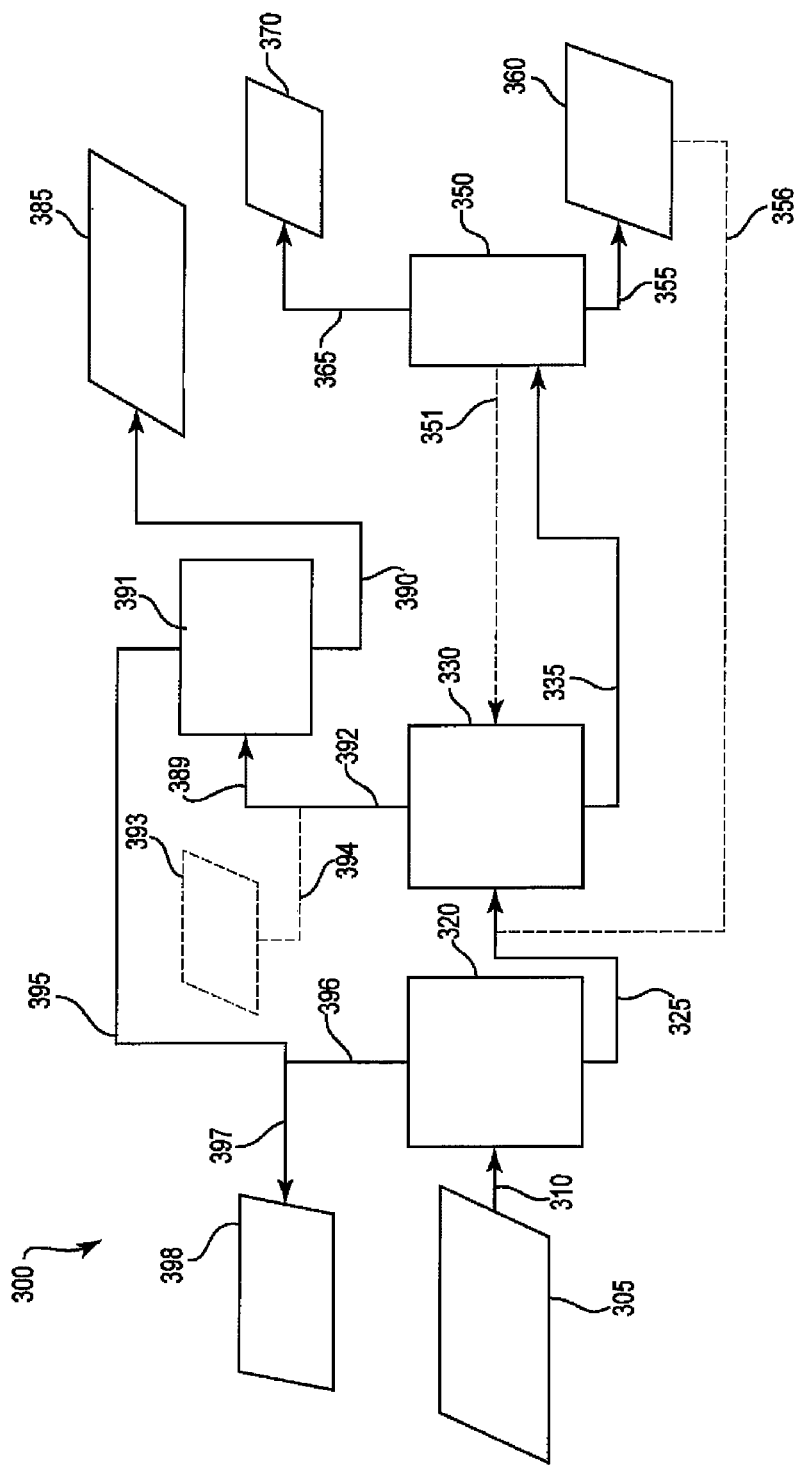
FIG. 3 shows a block diagram schematically illustrating a system for separating ethyleneamines from alkylethyleneamines according to yet another embodiment of the present invention.

FIG. 3 shows a block diagram schematically illustrating a system 300 for separating alkylethyleneamines from ethyleneamines according to another embodiment of the present invention. System 300 is similar to system 200 but advantageously eliminates water column 240. Eliminating an entire unit operation such as water column 240 can provide a substantial cost savings with respect to capital and/or operating expenditures.

A crude ethyleneamines stream 310 is provided from reactor 305. Stream 310 includes ethyleneamines, alkylethyleneamines, a first adjuvant component including water, and a second adjuvant component including ammonia. 320 represents flash tanks or an ammonia forecolumn, which operates to remove at least part of the ammonia.

Stream 325 is delivered to distillation column 330 which is operated according to the present invention to create a byproduct component that has an enhanced separation characteristic to help separate the alkylethyleneamines from the ethyleneamines. Stream 325 includes ethyleneamines, alkyethyleneamines, a first adjuvant component including water, and a second adjuvant component including ammonia. At least part of the alkylethyleneamines, water, and ammonia are separated from the ethyleneamines in column 330 and exit column 330 via stream 392.

The overhead stream 392 includes water, ammonia, and alkylethyleneamines. Stream 392 can optionally be combined with stream 394 from water source 393 to form stream 389. Stream 389 is delivered to an ammonia purification column 391. The overhead stream 395 includes ammonia (and does not include ethyleneamine) and can be combined with overhead stream 396 from flash tanks or forecolumn 320 and delivered to a recycle stream or reactor 398 via stream 397. Bottom stream 390 includes water and alkylethyleneamines that can be delivered to waste treatment process 385.

Stream 335 is thus enriched in the ethyleneamines and is delivered to column 350 for separating the ethyleneamines. In contrast to column 230, column 330 is operated so as to remove substantially more (sometimes substantially all) of the water from the ethyleneamines. In such embodiments, water column 240 is not needed. Optionally, column 350 can remove any remaining water (typically with a small amount of one or more ethyleneamines since they can form an azeotrope with water) and recycle it via stream 351. As an example, overhead stream 365 can include ethylenediamine (EDA) or EDA and piperazine (PIP) and be delivered to storage or final processing 370. Stream 355 can include heavier ethyleneamines that are delivered to additional refining processes 360. Optionally, at least a portion of the heavier ethyleneamines can be recycled via stream 356.

EXAMPLES

Example 1

Example 1 illustrates how alkylethylenediamines can be separated from ethylenediamine (EDA) according to the present invention using a first adjuvant component that includes water and a second adjuvant component that includes ammonia. Example 1 is explained using FIG. 3. A stream containing 0.101% by weight N-Ethylethylenediamine (EtEDA), 0.217% by weight N-Methylethylenediamine (MeEDA), 20.706% by weight ethylenediamine (EDA) 13.840% by weight Water, 7.335% by weight Ammonia and 57.802% of other ethanolamines and ethyleneamines (stream 325) is fed to a column (330). The column contains 71 trays (numbered top to bottom with the bottom or lowest tray numbered 71) and the column feed is introduced at tray 15. With the column 330 operating at head pressure of 179 kPa (26 psia), a head temperature of 102 C and a base temperature 180 C, the composition of the overhead make (from a total condenser is 34.091% Ammonia, 64.294%% Water, 0.442% EtEDA 0.974% Me EDA and 0.198% EDA (stream 392). At the conditions in the base of the water column, the bottoms stream 335 from the column 330 will contain 1.2% water. Stream 106 is then feed into an EDA column 350 containing 46 trays (numbered top to bottom with the bottom or lowest tray numbered 46) with the feed going to tray 34. The EDA Column runs with a head pressure of 21 kPa (160 mmHg) with a head temperature of 75 C and a base temperature of 144 C. EDA product Stream 365 is removed overhead in column 350 and has a composition of 0.026% by weight EtEDA, 0.036% by weight MeEDA, 99.900% by weight EDA 0.035% by weight Water and 0.002% of other ethanolamines and ethyleneamines. The water contained in stream 335 entering column 350 is removed from a side draw 351 on tray 27 and returned to tray 38 of column 330.

The resultant EDA product in destination 370 contains 626 parts per million by weight alkylethylenediamine. Comparatively, if the water and ammonia is not used in manner according to the present invention to help separate the alkylethylenediamines from ethylenediamine, the alkylethylenediamine content in the EDA product is 15,000 parts per million by weight alkylethylenediamine making the EDA material unacceptable for many applications.

Example 2

Example 2 illustrates how alkylethylenediamines can be separated from ethylenediamine (EDA) according to the present invention using a first adjuvant component that includes water and a second adjuvant component that includes ammonia. Example 2 is explained using FIG. 2. A stream containing 0.0264% by weight N-Ethylethylenediamine (EtEDA), 0.0570% by weight N-Methylethylenediamine (MeEDA), 20.7543% by weight ethylenediamine (EDA) 13.8725% by weight Water, 7.3524% by weight Ammonia and 57.9375% of other ethanolamines and ethyleneamines (stream 225) is fed to a column (230). A stream containing only water (stream 294) is also added to the condenser of column 230 as needed to ensure total condensation of ammonia. The column contains 23 trays (numbered top to bottom with the bottom or lowest tray numbered 23) and the column feed is introduced at tray 16. With the column 230 operating at head pressure of 179 kPa (26 psia), a head temperature of 105 C and a base temperature 129 C, the composition of the overhead make (from a total condenser is 34.2837% Ammonia, 65.2325%% Water, 0.0894% EtEDA, 0.1918% Me EDA and 0.2026% EDA (stream 292). Stream 235 is then feed into a water column (240) containing 78 trays (numbered top to bottom with the bottom or lowest tray numbered 78) with the feed going to tray 11. The water column runs with a head pressure of 400 kPa (58 psia), a head temperature of 143 C and a reboiler temperature of 210 C. A water free stream (245) is removed from the column base of column 240 and has a composition of 0.0046% by weight N-Ethylethylenediamine (EtEDA), 0.0124% by weight N-Methylethylenediamine (MeEDA), 26.3040% by weight ethylenediamine (EDA) 0.0092% by weight Water, 73.5870% of other ethanolamines and ethyleneamines. Stream 245 is then fed to EDA column 250 containing 46 trays (numbered top to bottom with the bottom or lowest tray numbered 46) with the feed going to tray 34. The EDA Column runs with ahead pressure of 21 kPa (160 mmHg) with a head temperature of 75 C and a base temperature of 143 C. EDA product Stream 265 is removed overhead in column 250 and has a composition of 0.0172% by weight EtEDA, 0.0469% by weight MeEDA, 99.2000% by weight EDA 0.348% by weight Water and 0.3878% of other ethanolamines and ethyleneamines.

The resultant EDA product 265 contains 641 parts per million by weight alkylethylenediamine. Comparatively, if the water and ammonia is not used in manner according to the present invention to help separate the alkylethylenediamines from ethylenediamine, the alkylethylenediamine content in the EDA product is approximately 4,000 parts per million by weight alkylethylenediamine making the EDA material unacceptable for some applications.

What is claimed is:
1. A process for separating one or more amine byproducts from one or more desired amines comprising the steps of:
  a) providing a composition comprising i) one or more desired amines selected from alkyleneamines represented by (a) formula (I):

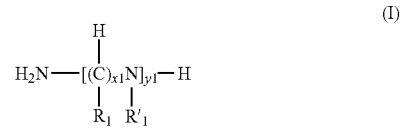

wherein $x_1$ is a number of from 2 to 6, $y_1$ is a number of from 1 to 6, $R_1$ represents a hydrogen atom or an alkyl group having 1 to 4 carbon atoms, and $R'_1$ represents a group represented by the following formula (1):

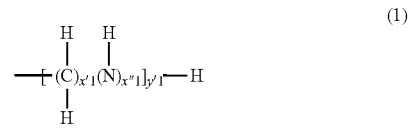

wherein $x'_1$ is a number of from 2 to 6, $x''_1$ is 0 or 1 and $y'_1$ is a number of from 0 to 4 and formula (II):

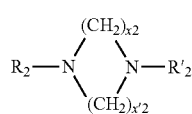

(II)

wherein $x_2$ and $x'_2$ are numbers of from 2 to 6, and $R_2$ and $R'_2$ represent a group represented by the following formula (2):

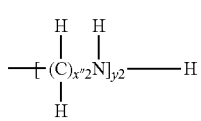

(2)

wherein $x''_2$, is a number of from 2 to 6 and $y_2$ is a number of from 0 to 5, and one or more amine byproducts and ii) a first adjuvant component, wherein the first adjuvant component has a boiling point;

b) causing the composition to be subjected to conditions such that at least a portion of the one or more amine byproducts and at least a portion of the first adjuvant component form a byproduct component that has an enhanced separation characteristic relative to the one or more amine byproducts that have not been subjected to said conditions; and c) separating at least a portion of the byproduct component from the composition in the presence of a second adjuvant component.

2. The process according to claim 1, wherein the second adjuvant component has a boiling point less than the boiling point of the first adjuvant component.

3. The process according to claim 1, wherein the one or more desired amines comprise one or more alkyleneamines and the one or more amine byproducts comprise one or more alkylalkyleneamines.

4. The process according to claim 3, wherein the one or more alkyleneamines comprise one or more ethyleneamines and the one or more alkylalkyleneamines comprise one or more alkylethyleneamines.

5. The process according to claim 1, wherein the first adjuvant component comprises an adjuvant selected from the group consisting of water, one or more hydrocarbons, lower alkylene glycols, monoalkyl ethers of alkylene glycol, dialkyl ethers of akylene glycol, lower aliphatic alcohols, and combinations thereof.

6. The process according to claim 1, wherein the second adjuvant component comprises an adjuvant selected from the group consisting of: ammonia, diatomic hydrogen, diatomic nitrogen, methane, methylamine, ethylamine, carbon dioxide, and combinations thereof.

7. A process for separating one or more alkylethyleneamines from one or more ethyleneamines comprising the steps of:

a) providing a composition comprising i) one or more ethyleneamines selected from monoethanolamine, diethanolamine, triethanolamine, 1,3-diaminopropane, dipropylenetriamine, 1,3-pentanediamine, 1,3-butanediamine, 2,2-dimethyl-1,3-propanediamine, 2,2-diethyl-1,3-propanediamine, ethylenediamine, diethylenetriamine, triethylenetetramine, tetraethylenepentamine, piperazine, aminoethylpiperazine, aminoethylethanolamine, heavy polyamine, and combinations thereof, and one or more alkylethyleneamines and ii) a first adjuvant component comprising water, wherein the first adjuvant component has a boiling point;

b) causing the composition to be subjected to conditions such that at least a portion of the one or more alkylethyleneamines and at least a portion of the first adjuvant component form an alkylethyleneamines component that has an enhanced separation characteristic relative to the one or more alkylethyleneamines that have not been subjected to said conditions; and c) separating at least a portion of the alkylethyleneamines component from the composition in the presence of a second adjuvant component.

8. The process according to claim 7, wherein the second adjuvant component comprises ammonia and has a boiling point less than the boiling point of the first adjuvant component.

9. The process according to claim 7, wherein the composition comprises an effluent from one or more processes that form the one or more ethyleneamines and the one or more alkylethyleneamines.

10. The process according to claim 7, wherein, after the separating step, the composition comprises:

a) one or more alkylethyleneamines in an amount of 0.5 percent or less by weight of the total composition;

b) water in an amount of 2 percent or less by weight of the total composition, and c) ammonia in an amount of 0.1 percent or less by weight of the total composition.

11. The process according to claim 7, wherein the separating step is a first separating step and further comprising a second separating step, wherein the second separating step comprises separating the water from the composition so that the composition comprises water in an amount of 0.5 percent or less by weight of the total composition.

12. A process for separating one or more amine byproducts from one or more desired amines comprising the steps of:

a) providing a composition comprising i) one or more desired amines selected from alkyleneamines represented by (a) formula (I):

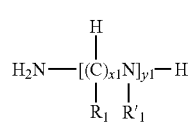

(I)

wherein $x_1$ is a number of from 2 to 6, $y_1$ is a number of from 1 to 6, $R_1$ represents a hydrogen atom or an alkyl group having 1 to 4 carbon atoms, and $R'_1$ represents a group represented by the following formula (1):

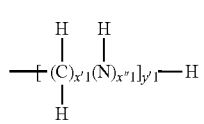

(1)

wherein $x'_1$ is a number of from 2 to 6, $x''_1$ is 0 or 1 and $y'_1$ is a number of from 0 to 4 and formula (II):

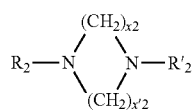

(II)

wherein $x_2$ and $x'_2$ are numbers of from 2 to 6, and $R_2$ and $R'_2$ represent a group represented by the following formula (2):

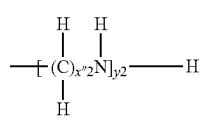

(2)

wherein $x''_2$ is a number of from 2 to 6 and $y_2$ is a number of from 0 to 5, and one or more amine byproducts and ii) a first adjuvant component, wherein the composition does not include water in an amount of more than one percent by weight of the total composition;

b) causing the composition to be subjected to conditions such that at least a portion of the one or more amine byproducts and at least a portion of the first adjuvant component form a byproduct component that has an enhanced separation characteristic relative to the one or more amine byproducts that have not been subjected to said conditions; and c) separating at least a portion of the byproduct component from the composition.

13. The process according to claim 12, wherein the first adjuvant component has a boiling point, wherein the separating step comprises separating at least a portion of the byproduct component from the composition in the presence of a second adjuvant component, wherein the second adjuvant component has a boiling point less than the boiling point of the first adjuvant component.

14. The process according to claim 12, wherein the one or more desired amines comprise one or more alkyleneamines and the one or more byproducts comprise one or more alkylalkyleneamines.

15. The process according to claim 14, wherein the one or more alkyleneamines comprise one or more ethyleneamines selected from monoethanolamine, diethanolamine, triethanolamine, 1,3-diaminopropane, dipropylenetriamine, 1,3-pentanediamine, 1,3-butanediamine, 2,2-dimethyl-1,3-propanediamine, 2,2-diethyl-1,3-propanediamine, ethylenediamine, diethylenetriamine triethylenetetramine tetraethylenepentamine, piperazine, aminoethylpiperazine, aminoethylethanolamine, heavy polyamine, and combinations thereof, and the one or more alkylalkyleneamines comprise one or more alkylethyleneamines.

16. The process according to claim 1 wherein the desired amine is ethylenediamine and the amine byproduct is selected from N-ethyletnylenediamine and N-methylethylenediamine.

17. The method according to claim 16 wherein the first adjuvant is water and the second adjuvant is ammonia.

* * * * *